(12) United States Patent
Lange (10) Patent No.: US 10,647,656 B2
(45) Date of Patent: May 12, 2020

(54) ETHANE OXIDATIVE DEHYDROGENATION WITH CO-PRODUCTION OF VINYL ACETATE

(71) Applicant: SHELL OIL COMPANY, Houston, TX (US)

(72) Inventor: Jean Paul Andre Marie Joseph Ghislain Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/470,462

(22) PCT Filed: Dec. 18, 2017

(86) PCT No.: PCT/EP2017/083226
§ 371 (c)(1),
(2) Date: Jun. 17, 2019

(87) PCT Pub. No.: WO2018/114752
PCT Pub. Date: Jun. 28, 2018

(65) Prior Publication Data
US 2020/0010400 A1   Jan. 9, 2020

(30) Foreign Application Priority Data
Dec. 19, 2016   (EP) ..................... 16204951

(51) Int. Cl.
*C07C 67/29*   (2006.01)
*C07C 67/48*   (2006.01)

(52) U.S. Cl.
CPC .............. *C07C 67/29* (2013.01); *C07C 67/48* (2013.01)

(58) Field of Classification Search
CPC .......... C07C 69/15; C07C 67/29; C07C 67/48
See application file for complete search history.

(56) References Cited

U.S. PATENT DOCUMENTS 7,390,918 B2 *   6/2008   Clarke .................... C07C 5/48
560/247

* cited by examiner

*Primary Examiner* — Paul A Zucker (57) ABSTRACT

The invention relates to an integrated process for the production of ethylene and vinyl acetate (VAM), comprising contacting in a first reaction zone a gas stream comprising ethane and optionally ethylene with an oxygen-containing gas stream in the presence of a oxydehydrogenation catalyst under oxidative dehydrogenation conditions to produce a first product stream comprising ethane, ethylene, acetic acid and water, and optionally other compounds, separating said first product stream in a vapor permeation unit into a second stream comprising water and a third stream comprising ethane, ethylene, acetic acid, and optionally other gaseous compounds, contacting in a second reaction zone all or at least a portion of said third stream with a stream comprising concentrated acetic acid and with an oxygen-containing gas stream in the presence of a VAM catalyst, to produce a fourth product stream comprising vinyl acetate, acetic acid, ethane, ethylene, water, carbon dioxide, and optionally other compounds, separating said fourth product stream in a vinyl acetate separation zone into a fifth stream comprising vinylacetate, acetic acid, water and optionally other condensable compounds, and a sixth stream comprising ethylene, ethane, carbon dioxide and optionally other gaseous compounds, and recovering vinyl acetate from said fifth stream. The invention further relates to a reaction system for carrying out the process.

12 Claims, 3 Drawing Sheets

ETHANE OXIDATIVE DEHYDROGENATION WITH CO-PRODUCTION OF VINYL ACETATE

CROSS REFERENCE TO RELATED APPLICATIONS

This is a national stage application of International Application No. PCT/EP2017/083226, filed 18 Dec. 2017, which claims benefit of priority to European Patent Application No. 16204951.4, filed 19 Dec. 2016.

Field of the Invention

The present invention relates to integrated process and system for the oxidative conversion of ethane to ethylene and vinyl acetate.

BACKGROUND OF THE INVENTION

It is known to oxidatively dehydrogenate alkanes, such as ethane, to produce ethylene in an oxidative dehydrogenation (oxydehydrogenation; ODH) process. Examples of ethane ODH processes, including catalysts and other process conditions, are disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) can be used as such oxydehydrogenation catalysts. The dehydrogenated equivalent of ethane may be further oxidized under the same conditions into acetic acid.

Presently, the process can achieve over 90% ethylene selectivity to ethylene at over 50% conversion. The process is also typically producing acetic acid (AA, ~5 mol % selectivity) together with carbon dioxide ($CO_2$).

In the above processes, the acetic acid thus produced is generally considered as waste products. Although they could be condensed together with water from the reactor effluent as an aqueous carboxylic acid (ca. 10 wt %) stream, the low relative volatility of carboxylic acids to water renders distillative separation of carboxylic acid and water troublesome, as this would require very large condensate recycle and/or separation trains.

Accordingly, current ODH processes are designed for minimal acetic acid co-production. However, proper valorization of acetic acid could allow "relaxing" acetic acid specifications, thereby widening the operating window to accommodate e.g. higher pressures, lower temperatures and/or easier management of heat release and explosion risks in the ODH process. For example, relaxing the acetic acid specification to 10 mol % selectivity could deliver an aqueous side-stream containing 20 wt % acetic acid.

WO1998005620 describes an integrated process for the production of acetic acid and/or vinyl acetate which comprises the steps: (a) contacting in a first reaction zone a gaseous feedstock comprising ethylene and/or ethane and optionally steam with a molecular oxygen-containing gas in the presence of a catalyst active for the oxidation of ethylene to acetic acid and/or ethane to acetic acid and ethylene to produce a first product stream comprising acetic acid, water and ethylene (either as unconverted ethylene and/or as co-produced ethylene) and optionally also ethane, carbon monoxide, carbon dioxide and/or nitrogen; (b) contacting in a second reaction zone in the presence or absence of additional ethylene and/or acetic acid at least a portion of the first gaseous product stream comprising at least acetic acid and ethylene and optionally also one or more of water, ethane, carbon monoxide, carbon dioxide and/or nitrogen with a molecular oxygen-containing gas in the presence of a catalyst active for the production of vinyl acetate to produce a second product stream comprising vinyl acetate, water, acetic acid and optionally ethylene; (c) separating the product stream from step (b) by distillation into an overhead azeotrope fraction comprising vinyl acetate and water and a base fraction comprising acetic acid; (d) either (i) recovering acetic acid from the base fraction separated in step (c) and optionally recycling the azeotrope fraction separated in step (c) after partial or complete separation of the water therefrom to step (c), or (ii) recovering vinyl acetate from the azeotrope fraction separated in step (c) and optionally recycling the base fraction separated in step (c) to step (b), or (iii) recovering acetic acid from the base fraction separated in step (c) and recovering vinyl acetate from the overhead azeotrope fraction recovered in step (c).

WO2000069802 describes a process for the production of vinyl acetate monomer comprising the steps of: (1) contacting a gaseous feed mixture of ethane or ethylene or ethane/ethylene, steam and a molecular oxygen containing gas in the presence of a first catalyst active for oxidation of ethane, ethylene or ethane/ethylene to produce a selective stream of acetic acid, ethylene, carbon dioxide and water and (2) converting a second feed mixture comprising ethylene, acetic acid and oxygen to vinyl acetate monomer in the presence of a second catalyst active for the production of vinyl acetate, wherein said process does not include an intermediate separation step to remove the CO between the two reaction steps.

WO2001090042 describes an integrated process for the production of vinyl acetate which comprises the steps of: a) contacting in a first reaction zone a gaseous feedstock comprising essentially ethane with a molecular oxygen-containing gas in the presence of a catalyst to produce a first product stream comprising acetic acid and ethylene; b) contacting in a second reaction zone the first gaseous product stream with a molecular oxygen-containing gas in the presence of a catalyst to produce a second product stream comprising vinyl acetate; c) separating the product stream from step (b) and recovering vinyl acetate from the product stream from step (b).

These prior art processes generally suffer from poor selectivity to vinyl acetate due to the presence of considerable amounts of water in the effluent of the oxidative dehydrogenation reaction.

It is desirable to provide an ethane oxidative dehydrogenation process, wherein the acetic acid side stream thus produced is valorized by conversion to vinyl acetate in a technically advantageous, efficient and economically affordable manner.

SUMMARY OF THE INVENTION

It was surprisingly found that the above-mentioned objective can be attained by means of an integrated process, wherein the effluent of a first ethane oxidative dehydrogenation [oxydehydrogenation; (E)ODH] step is dewatered, an wherein at least part of the dewatered ethylene and acetic acid are further converted in a second ("VAM") process to vinyl acetate (also referred to in the art as vinyl acetate monomer or simply "VAM").

Accordingly, in a first aspect the present invention pertains to an integrated process for the production of ethylene and vinyl acetate (VAM), comprising contacting in a first reaction zone a gas stream comprising ethane and optionally ethylene with an oxygen-containing gas stream in the presence of a oxydehydrogenation catalyst under oxidative dehydrogenation conditions to produce a first product stream comprising ethane, ethylene, acetic acid and water, and optionally other compounds, separating said first product stream in a vapor permeation unit into a second stream comprising water and a third stream comprising ethane, ethylene, acetic acid, and optionally other gaseous compounds, contacting in a second reaction zone all or at least a portion of said third stream with a stream comprising concentrated acetic acid and with an oxygen-containing gas stream in the presence of a VAM catalyst, to produce a fourth product stream comprising vinyl acetate, acetic acid, ethane, ethylene, water, carbon dioxide, and optionally other compounds, separating said fourth product stream in a vinyl acetate separation zone into a fifth stream comprising vinylacetate, acetic acid, water and optionally other condensable compounds, and a sixth stream comprising ethylene, ethane, carbon dioxide and optionally other gaseous compounds, and recovering vinyl acetate from said fifth stream.

In another aspect, the invention relates to reaction system for the oxidative dehydrogenation of ethane and co-production of vinyl acetate, comprising a first reaction zone, having
an inlet for receiving an ethane-containing feed stream,
an inlet for receiving an oxygen-containing feed stream, and
an outlet for discharging an effluent from the first reaction zone,
a vapor permeation unit, having
an inlet for receiving an effluent from the first reaction zone,
an outlet for discharging a water-depleted effluent stream from the vapor permeation unit, and
an outlet for discharging water from the vinyl acetate separation zone,
a second reaction zone, having
an inlet for receiving the water-depleted effluent stream from the vapor permeation unit,
an inlet for receiving an oxygen-containing feed stream,
an inlet for receiving a concentrated acetic acid-containing feed stream, and
an outlet for discharging an effluent from the second reaction zone,
a vinyl acetate separation zone, having
an inlet for receiving an effluent from the second reaction zone,
optionally an inlet for receiving a washing liquid stream,
an outlet for discharging a vinyl acetate-enriched liquid stream from the vinyl acetate separation zone, and
an outlet for discharging a vinyl acetate-depleted gaseous stream from the vinyl acetate separation zone,
a purification zone, having
an inlet for receiving a vinyl acetate-enriched liquid stream from the vinyl acetate separation zone,
an outlet for discharging a concentrated acetic acid-containing stream from the purification zone, and,
an outlet for discharging a concentrated vinyl acetate-containing stream from the purification zone, and
one or more outlets for discharging further compounds, and
optionally, a carbon dioxide removal zone, having an inlet for receiving a vinyl acetate-depleted gaseous stream from the vinyl acetate separation zone, and
an outlet for discharging a carbon dioxide-depleted stream from said carbon dioxide removal zone, and,
optionally, an ethane/ethylene separation unit, having
an inlet for receiving a carbon dioxide-depleted gaseous stream from the carbon dioxide removal zone,
an outlet for discharging an ethylene-enriched stream from said ethane/ethylene separation unit, and
an outlet for discharging an ethane-enriched stream from said ethane/ethylene separation unit.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION OF THE INVENTION

While the process of the present disclosure and the streams used in said process are described in terms of "comprising", "containing" or "including" one or more various described steps and components, respectively, they can also "consist essentially of" or "consist of" said one or more various described steps and components, respectively.".

The term "at least a portion of", as used herein, may in particular mean at least 1% thereof, in particular at least 2.5% thereof, in particular at least 5% thereof, in particular at least 10% thereof, in particular at least 15% thereof, in particular at least 20% thereof, in particular at least 25% thereof, in particular at least 30% thereof, in particular at least 35% thereof, in particular at least 40% thereof, in particular at least 45% thereof, in particular at least 50% thereof, in particular at least 55% thereof, in particular at least 60% thereof, in particular at least 65% thereof, in particular at least 70% thereof, in particular at least 75% thereof, in particular at least 80% thereof, in particular at least 85% thereof, in particular at least 90% thereof, in particular at least 95% thereof, in particular at least 98% thereof, and may also mean at least 99% thereof.

The present disclosure relates to a process and reaction system for the oxidative dehydrogenation of ethane, and conversion of at least part of the effluent of said dehydrogenation process to vinyl acetate. The process and the apparatus as described herein allow utilizing the effluent of an ethane oxidative dehydrogenation (ODH) process comprising relatively high concentrations of acetic acid in an efficient manner, thereby producing ethylene and vinyl acetate monomer (VAM) as valuable chemicals, while minimizing losses of ethylene in purge streams. The process and the reaction system as described herein allow significant integration of the ODH and VAM processes, with the possibility of sharing several common process units, such as oxygen supply, carbon dioxide removal and acetic acid drying/recovery, thus further contributing to the overall cost-effectiveness of the present disclosure. An additional advantage of the process a disclosed herein is that there is no need to remove remaining oxidizing agent, if any, from the product stream resulting from the oxydehydrogenation step, since oxidizing agent is also required in the subsequent production of vinylacetate.

In the oxidative dehydrogenation part of the present process, a gas stream comprising oxygen ($O_2$) and a gas stream comprising ethylene are contacted with a mixed metal oxide oxydehydrogenation catalyst typically comprising molybdenum, vanadium, niobium and optionally tellurium. The effluent stream of this oxidative dehydrogenation step generally comprises unreacted ethane, ethylene, water of reaction, acetic acid, and optionally also unreacted oxygen, carbon monoxide and carbon dioxide.

Water is formed in a molar ratio of at least 1:1 to ethylene during the conversion of ethane to ethylene. In the present disclosure, the ODH effluent stream comprising unconverted ethane, ethylene and water is fed to a vapor permeation unit, and water is removed from said effluent stream to produce a dewatered stream comprising ethylene and unconverted ethane.

In the vapor permeation unit, the vaporous ODH effluent stream is brought into contact with the active side of a ceramic or polymeric water-permeable membrane such that water passes through the membrane and is continuously removed in the form of vapor from the back (permeate) side of the membrane. The continuous removal of water vapor creates a concentration gradient across both sides of the pervaporation membrane, which acts as a driving force for the vapor permeation water removal process.

The vinylacetate (VAM) part of the present process generally involves contacting a gas stream comprising oxygen ($O_2$), all or at least a portion of the dewatered ethylene-containing effluent of the ODH process, and a (vaporous) stream comprising acetic acid in the presence of a VAM catalyst, typically a palladium-based catalyst, to produce an effluent typically comprising vinylacetate, unconverted ethylene, unconverted acetic acid, unconverted oxygen, water of reaction, carbon dioxide, and heavies such as acetaldehyde and ethyl (di)acetate.

In the process as disclosed herein, this effluent is separated, in a vinyl acetate separation zone, in a liquid stream comprising vinyl acetate, acetic acid, water and optionally other condensable compounds, and a gaseous stream comprising unconverted ethylene and/or ethane, carbon dioxide and optionally other gaseous compounds.

In one embodiment, the vinyl acetate separation zone comprises a condenser. Typically, said condenser comprises a cooling device and optionally one or more internals to enhance the formation of a continuous liquid phase.

In another embodiment, the vinyl acetate separation zone is a washing zone, wherein the fourth product stream is contacted with water or a liquid absorbent stream to produce a fifth stream comprising vinylacetate, acetic acid, water and/or absorbent and optionally other condensable compounds, and a sixth stream comprising ethylene, ethane, carbon dioxide, and optionally other gaseous compounds. As used herein, the term "washing" relates to contacting the vaporous VAM effluent with a "washing agent", such as water or (another) liquid absorbent, with the purpose of separating vinyl acetate and other condensables from said vaporous stream. Washing of said first stream can be performed in a washing column or by absorption in e.g. an absorption column, such that vinyl acetate, acetic acid, water and other condensable compounds are retained in the liquid phase and a gaseous stream comprising ethylene, ethane, carbon dioxide and optional other gaseous compounds, passes through.

In one embodiment, the liquid absorbent stream comprises or consists of acetic acid. In another embodiment, the liquid absorbent stream comprises or consists of water. In another embodiment, the liquid absorbent may be another liquid that is capable of absorbing vinyl acetate from the VAM effluent, and that is capable of being recovered from the purification zone as described below and, if desired, being recirculated (recycled) to the vinyl acetate separation zone. Examples of suitable liquid absorbents are typically oxygen-containing high-boiling organic solvents, including sulfolanes; glycols such as ethylene glycol and propylene glycol and their (di)acetates, ethers and diglycides; N-methylpyrrolidone; phenol and substituted phenols; as well as "heavies" that are also formed as by-products in the processes as disclosed herein, such as acetaldehyde, ethyl acetate, and combinations thereof. Suitably, these liquid absorbents are recovered in the vinyl acetate purification as described below, and at least partially recycled to the vinyl acetate separation ("washing") zone.

In one embodiment, the fifth stream is fed to a purification zone to produce a seventh stream comprising concentrated acetic acid, an eighth stream comprising concentrated vinyl acetate, and one or more streams comprising water and/or absorbent, and optionally other compounds such as acetaldehyde and ethyl acetate. In one embodiment, all or at least a portion of the seventh stream comprising concentrated acetic acid is used as the liquid absorbent stream in the washing zone as described above.

The presence of water in the VAM feed is undesirable as it leads to hydrolysis of vinylacetate to acetaldehyde and acetic acid. Since water is formed during the VAM reaction, acetic acid is typically dried by feeding it in the product work-up (purification) section, and the dried acetic acid may subsequently recirculated to the VAM reactor. Accordingly, in one embodiment all or at least a portion of the seventh stream comprising concentrated acetic acid is used as the feed stream comprising concentrated acetic acid supplied to the second reaction zone.

As mentioned above, the vaporous effluent from the VAM wash step generally comprises unconverted ethylene, unconverted ethane and carbon dioxide. Preferably, this stream is first subjected to a carbon dioxide removal step to produce a stream comprising ethylene and ethane, which may subsequently be split in a stream enriched in ethylene and a stream enriched in ethane. The stream enriched in ethylene may be withdrawn as product, and after optional further purification, be stored for sale or use in another conversion process. Alternatively or additionally, all or at least a portion of the stream enriched in ethylene may be recirculated to the VAM reaction step. Alternatively or additionally, all or at least a portion of the stream enriched in ethane may be recirculated to the ODH reaction step. Thus, in one embodiment, the sixth stream comprising ethylene and ethane, carbon dioxide, and optionally other gaseous compounds is fed to a carbon dioxide removal zone to remove carbon dioxide and optionally light condensable compounds, to produce an ninth stream enriched in ethane and ethylene. In one embodiment, all or at least a portion of said ninth stream enriched in ethane and ethylene is recirculated as feed to the first (ODH) reaction zone. In one embodiment, said ninth stream enriched in ethane and ethylene is further separated in an ethane/ethylene separation unit to produce a tenth stream enriched in ethane and a eleventh stream enriched in ethylene. In one embodiment, all or at least a portion of the tenth stream enriched in ethane is recirculated to the first reaction zone. In one embodiment, all or at least a portion of the eleventh stream enriched in ethylene is recirculated to the second reaction zone. Any combination of the above recirculation steps of streams enriched in ethane, ethylene or both is also possible.

In the ODH step of the process of the present invention, oxygen and ethane may be fed to the reactor together or separately. That is to say, one or more feed streams, suitably gas streams, comprising one or more of said 2 components may be fed to the reactor. For example, one feed stream comprising oxygen and ethane may be fed to the reactor. Alternatively, two or more feed streams, suitably gas streams, may be fed to the reactor, which feed streams may form a combined stream inside the reactor. For example, one feed stream comprising oxygen and another feed stream comprising ethane may be fed to the reactor separately. Further, in the ODH step of the process of the present invention, suitably during contacting oxygen and ethane with an ODH catalyst, the temperature is of from 300 to 500° C. More preferably, said temperature is of from 310 to 450° C., more preferably of from 320 to 420° C., most preferably of from 330 to 420° C.

Still further, in the above-mentioned ODH step, suitably during contacting the oxygen and ethane with an ODH catalyst, typical pressures are 0.1-30 or 0.1-20 bara (i.e. "bar absolute"). Further, preferably, said pressure is of from 0.1 to 15 bara, more preferably of from 1 to 8 bara, most preferably of from 3 to 8 bara. The product of the above-mentioned ODH step comprises the dehydrogenated equivalent of ethane, that is to say ethylene. Ethylene is initially formed in said step. However, in said same step, ethylene may be further oxidized under the same conditions into the corresponding carboxylic acid, that is to say acetic acid. In addition to oxygen and ethane, an inert gas may also be fed to the ODH reactor. Said inert gas may be selected from the group consisting of the noble gases and nitrogen (N2). Preferably, the inert gas is nitrogen or argon, more preferably nitrogen. Said oxygen is an oxidizing agent, thereby resulting in oxidative dehydrogenation of ethane. Said oxygen may originate from any source, such as for example air. Ranges for the molar ratio of oxygen to ethane which are suitable, are of from 0.01 to 1, more suitably 0.05 to 0.5. Said ratio of oxygen to ethane is the ratio before oxygen and ethane are contacted with the catalyst. In other words, said ratio of oxygen to ethane is the ratio of oxygen as fed to ethane as fed. Obviously, after contact with the catalyst, at least part of the oxygen and ethane gets consumed.

Oxidative dehydrogenation catalysts suitable for use in the present disclosure are not particularly limited and may include any ethane oxidative dehydrogenation (oxydehydrogenation) catalyst. The amount of such catalyst is not essential. Preferably, a catalytically effective amount of the catalyst is used, that is to say an amount sufficient to promote the ethane oxydehydrogenation reaction.

Examples of suitable oxidative dehydrogenation catalyst include, but are not necessarily limited to, one or more mixed metal oxide catalyst comprising molybdenum, vanadium, niobium and optionally tellurium as the metals and may have the following formula:

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

Optionally, a catalyst bed may comprise more than one oxidative dehydrogenation catalyst. For example, in one embodiment, a catalyst bed may comprise a plurality of oxidative dehydrogenation catalysts having varied activity levels (e.g. so as to vary the activity level along the length of the reactor tube). Further, if desired, the catalyst bed may further comprise inert material (e.g. to dilute and/or reduce the activity of the catalyst bed).

Preferably, the oxidative dehydrogenation catalyst is heterogeneous and in the form of particles. Further, preferably, said heterogeneous catalyst is porous, specifically a porous, particulate catalyst.

The ODH reactor that may be used in the above-mentioned ODH step may be any reactor, including fixed-bed and fluidized-bed reactors. Suitably, the reactor is a fixed-bed reactor. Examples of oxydehydrogenation processes, including catalysts and process conditions, are for example disclosed in above-mentioned U.S. Pat. No. 7,091,377, WO2003064035, US20040147393, WO2010096909 and US20100256432.

The VAM process as disclosed herein typically proceeds by co-feeding the stream comprising a vaporous acetic acid and ethylene in a preferred ethylene:acetic acid molar ratio in the range of 2:1 to 4:1, together with oxygen in a concentration of preferably at most 9 vol %, based on total volume of the VAM process gas feed, in the presence of a catalyst active for the production of vinyl acetate. Suitable catalysts for the oxidative conversion of ethylene and acetic acid to vinyl acetate are known in the art, and typically comprise unsupported or supported (e.g., on silica or alumina) palladium. Typically, suitable VAM catalysts further comprise one or more alkali metal promoters, for example sodium or potassium acetate, and an optional co-promoter such gold and/or cadmium. The pressure is typically in the range of 5 to 8 bara and the temperature is typically in the range of 100-250° C., preferably in the range of 160 to 180° C. Generally, acetate salt is co-fed with the acetic acid/ethylene feed in order to compensate for losses of the VAM catalyst alkali promoter. The VAM reactor that may be used in the above-mentioned ODH step may be any reactor, including fixed-bed and fluidized-bed reactors. Suitably, the reactor is a fixed-bed reactor.

The present disclosure further relates to a reaction system which is suitable for performing the ODH and VAM processes as disclosed herein, more in particular an integrated reaction system oxidative dehydrogenation (ODH) configuration and vinyl acetate (VAM) configuration, comprising a first reaction zone, having
   an inlet for receiving an ethane-containing feed stream,
   an inlet for receiving an oxygen-containing feed stream, and
   an outlet for discharging an effluent from the first reaction zone,
a vapor permeation unit, having
   an inlet for receiving an effluent from the first reaction zone,
   an outlet for discharging a water-depleted effluent stream from the vapor permeation unit, and an outlet for discharging water from the vinyl acetate separation zone,
a second reaction zone, having
an inlet for receiving the water-depleted effluent stream from the vapor permeation unit,
an inlet for receiving an oxygen-containing feed stream,
an inlet for receiving a concentrated acetic acid-containing feed stream, and
an outlet for discharging an effluent from the second reaction zone,
a vinyl acetate separation zone, having
an inlet for receiving an effluent from the second reaction zone,
optionally an inlet for receiving a washing liquid stream,
an outlet for discharging a vinyl acetate-enriched liquid stream from the vinyl acetate separation zone, and
an outlet for discharging a vinyl acetate-depleted gaseous stream from the vinyl acetate separation zone,
a purification zone, having
an inlet for receiving a vinyl acetate-enriched liquid stream from the vinyl acetate separation zone,
an outlet for discharging a concentrated acetic acid-containing stream from the purification zone, and,
an outlet for discharging a concentrated vinyl acetate-containing stream from the purification zone, and
one or more outlets for discharging further compounds, and
optionally, a carbon dioxide removal zone, having
an inlet for receiving a vinyl acetate-depleted gaseous stream from the vinyl acetate separation zone, and
an outlet for discharging a carbon dioxide-depleted stream from said carbon dioxide removal zone, and,
optionally, an ethane/ethylene separation unit, having
an inlet for receiving a carbon dioxide-depleted gaseous stream from the carbon dioxide removal zone,
an outlet for discharging an ethylene-enriched stream from said ethane/ethylene separation unit, and
an outlet for discharging an ethane-enriched stream from said ethane/ethylene separation unit.

Figure 1:
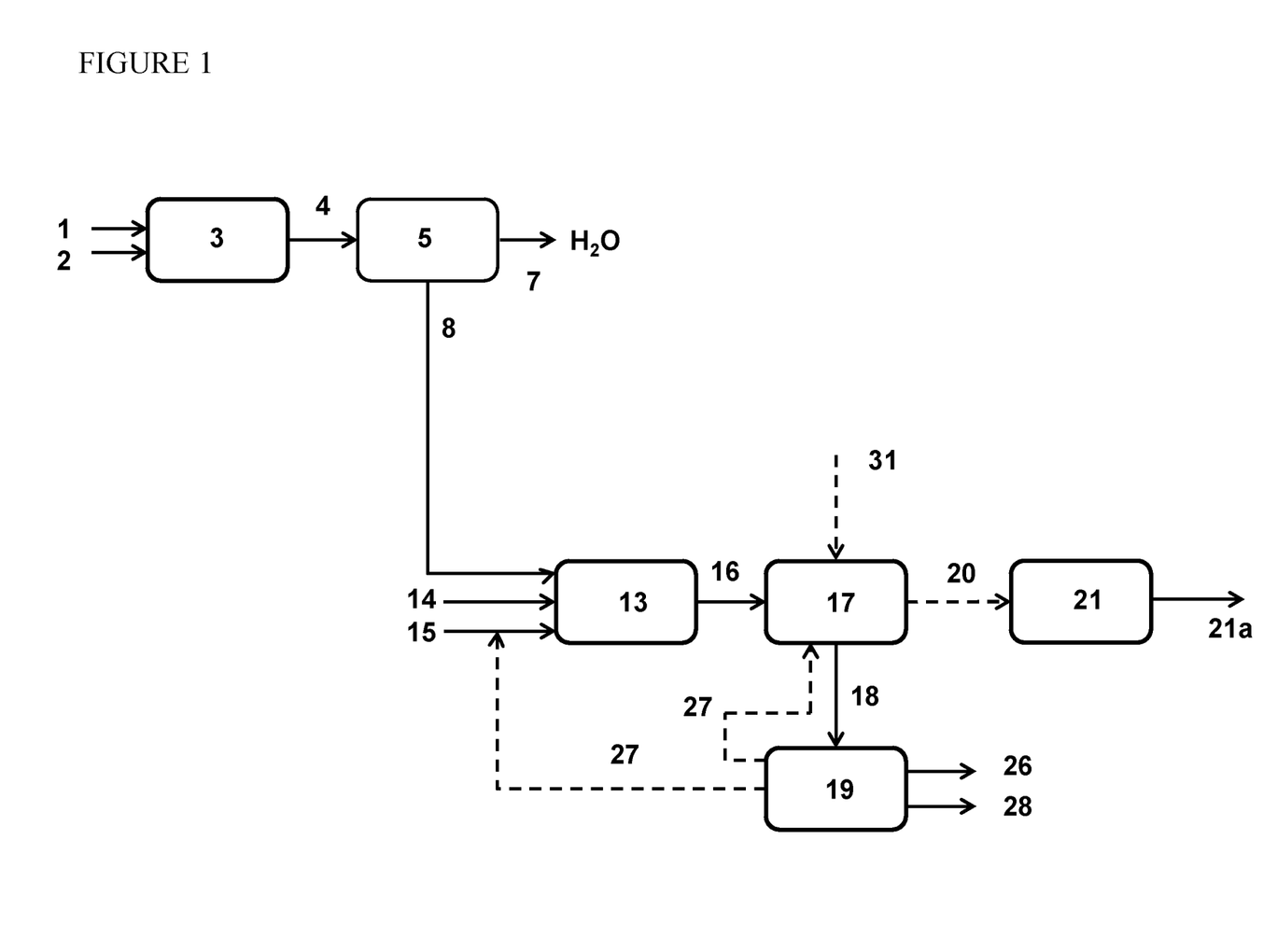
FIG. 1 shows an embodiment of the present invention.
Figure 2:
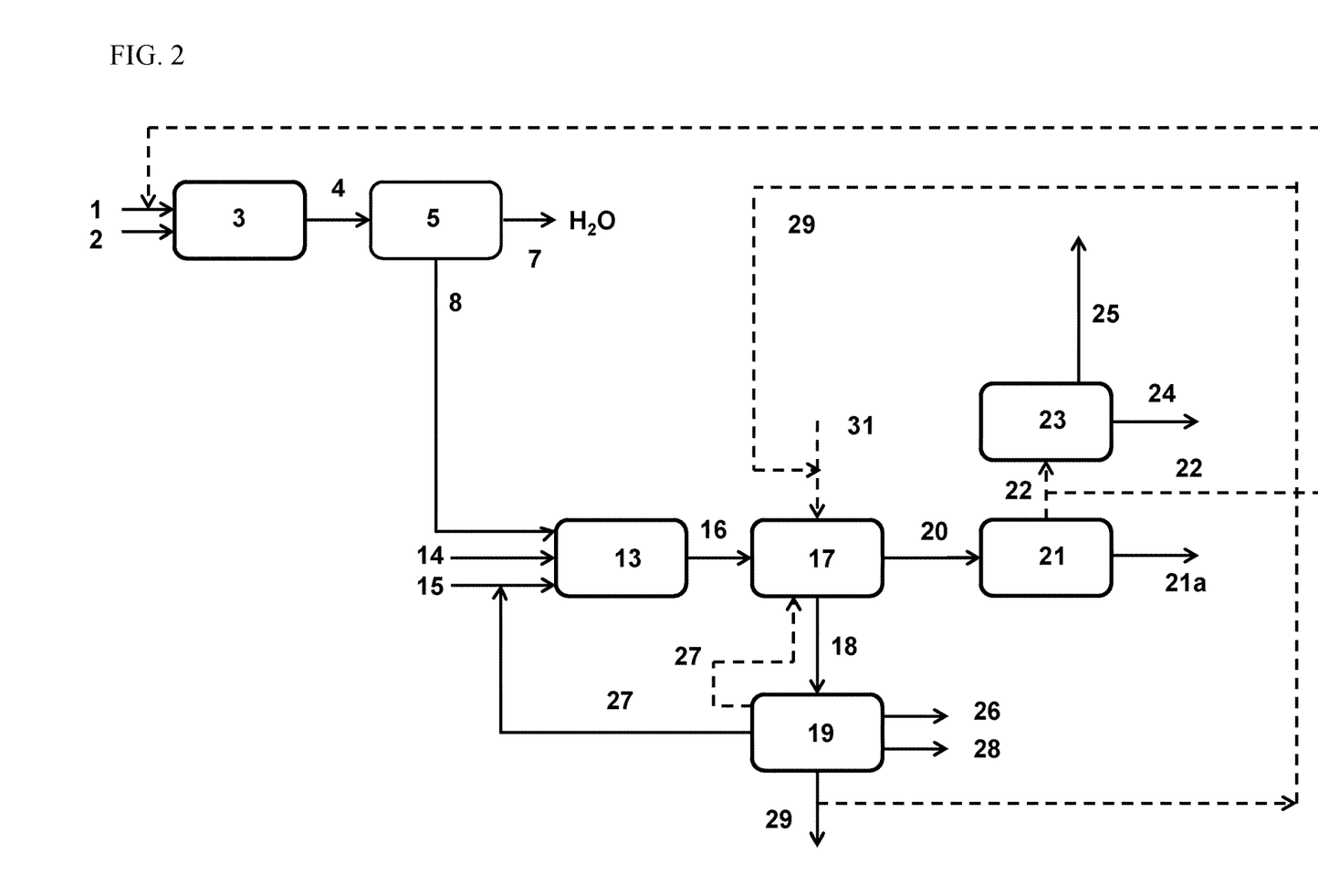
FIG. 2 shows an embodiment of the present invention with optional recirculation of absorbent and ethane/ethylene.
Figure 3:
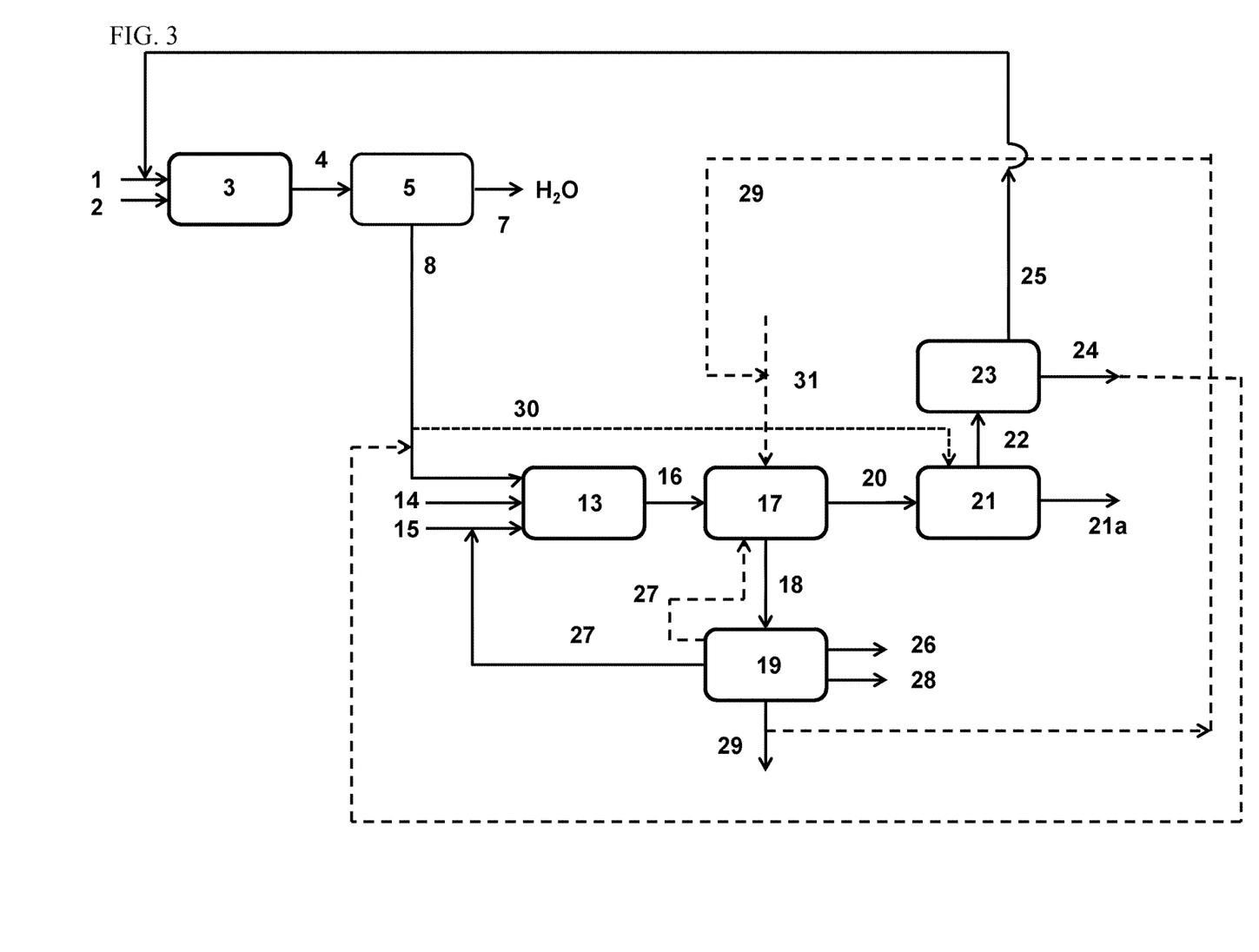
FIG. 3 shows an embodiment of the present invention with optional by-pass of the "VAM section".

As shown in FIGS. 1-3, the vinylacetate section comprising vinylacetate reaction unit (13), washing zone (17) and purification zone (19) may be inserted between vapor permeation unit (5) and CO2 removal unit (21) of an existing apparatus (plant) for oxidative dehydrogenation of alkanes.

Typically, such integration design involves means, such as by-pass line (30) for by-passing the vinylacetate reaction unit, allowing production, by means of oxidative dehydrogenation (only) under suitable conditions, of ethylene and acetic acid at market specification when the VAM process is down.

Accordingly, in one embodiment the apparatus as disclosed herein comprises means for by-passing the second reaction zone, said means comprising means for directly feeding the dewatered ODH effluent stream from vapor permeation unit (5) to the VAM separation zone and/or carbon dioxide removal zone (and subsequent ethane/ethylene separation unit). As used herein, such "means" typically comprise a conduit for fluidly connecting an outlet with an inlet of the referenced apparatuses and/or units, and may further comprise equipment for, e.g., compressing streams in such conduits, if necessary.

As used herein, "feeding directly to the VAM separation zone and/or carbon dioxide removal zone" should be understood to imply that no or substantially no effluent from the dewatering section is supplied to and reacted in the vinyl acetate reaction unit; it may still be possible though to have process units other than the VAM section units present between the ODH effluent vapor permeation unit and VAM separation zone and/or carbon dioxide removal zone.

In the present invention, any carbon dioxide may be removed from streams containing carbon dioxide by any one of well-known methods in a carbon dioxide removal zone comprising one or more carbon dioxide removal units. A suitable carbon dioxide removal agent that may be fed to a carbon dioxide removal unit may be an aqueous solution of a base, for example sodium hydroxide or an amine. After such carbon dioxide removal, the stream should be dried in a drying unit to remove residual water from the stream. Contacting an aqueous solution of an amine with a carbon dioxide containing stream is preferred in a case where the carbon dioxide amount is relatively high. Contacting an aqueous solution of sodium hydroxide with a carbon dioxide containing stream is preferred in a case where the carbon dioxide concentration is relatively low, or as second carbon dioxide removal step in the case of an ethane ODH effluent that was first treated with an aqueous solution of an amine and which still contains some residual carbon dioxide.

The vinyl acetate purification zone will generally a combination of apparatuses configured for (azeotropic) distillation of vinylacetate and water, followed by decanting and purification, and removal of the lights (acetaldehyde) and heavies (ethyl (di)acetate) by distillation.

Separation of ethane from ethylene in the carbon dioxide-depleted ("ninth") gaseous stream produced in the VAM reaction step is typically performed using cryogenic distillation, wherein said stream is cooled until it liquefies and subsequently distilled at the various boiling temperatures of the components. Other suitable, non-cryogenic, ethane/ethylene separation methods include pressure-swing and temperature-swing absorption, wherein components of the gaseous stream are selectively adsorbed on or absorbed by an absorbent or adsorbent material depending on their affinity for said material at the prevailing pressure or temperature, respectively, and selectively desorbed by changing said pressure or temperature; membrane permeation, which is based on the difference in rate of permeation through a membrane; and combinations of such methods, such as pressure swing permeation.

The vapor permeation unit can be any vapor permeation apparatus that is capable of selectively removing water from the vaporous effluent stream of the first 9ODH) reaction zone, and the skilled person will be capable of selecting appropriate membrane materials and temperature and pressure conditions.

As used herein, the washing zone can be any apparatus that is capable of contacting a gaseous or vaporous VAM effluent stream with water or another liquid absorbent stream with the purpose of separating vinyl acetate and other condensables. This may, for example, be an absorption or washing column having inlets for receiving a VAM effluent stream and for an absorbent stream, wherein the effluent stream is fed into the lower zone of a packed or tray column and the liquid absorbent is fed into the upper zone of the column, and wherein the vinyl acetate is absorbed by the absorbent via direct contact of the rising vapour stream and the falling absorbent.

The reaction system as disclosed herein may further comprise means for recirculating the concentrated acetic acid-containing stream from the purification zone to the second reaction zone or to the vinyl acetate (VAM) separation zone.

The reaction system as disclosed herein may further comprise means for recirculating recovered absorbent from the purification zone to the vinyl acetate (VAM) separation zone.

The reaction system as disclosed herein may further comprise means for recirculating an ethylene-containing stream from the ethane/ethylene separation unit to the second reaction zone.

The reaction system as disclosed herein may further comprise means for recirculating an ethane-containing stream from the ethane/ethylene separation unit to the first reaction zone.

The reaction system as disclosed herein may further comprise means for recirculating the carbon dioxide-depleted gaseous stream from the carbon dioxide removal zone to the first reaction zone.

Combinations of two or more of the above embodiments also fall within the scope of the present disclosure.

DETAILED DESCRIPTION OF THE DRAWINGS

FIG. 1 is a schematic view of a flow scheme for the oxidative hydrogenation of ethylene and production of vinyl acetate, according to an embodiment of the present disclosure. In the flow scheme of FIG. 1, a stream (1) comprising ethane and an oxygen-comprising stream (2) are fed to the first reaction (oxydehydrogenation) unit (3). A stream (4) comprising ethylene, unconverted ethane, acetic acid and water leaves the oxydehydrogenation unit (3), and is supplied to a vapor permeation unit (5) to produce a water vapor stream (7) and a dewatered stream (8) comprising ethylene, ethane and acetic acid. Dewatered stream (8) comprising ethylene, ethane and acetic acid is supplied to second reaction (vinylacetate; "VAM") unit (13), as well as oxygen-containing stream (14). A stream (15) comprising concentrated acetic acid is also supplied to vinylacetate reaction unit (13). This stream (15) comprising concentrated acetic acid may comprise concentrated acetic acid obtained as stream (27) from the vinyl acetate purification section.

The effluent stream (16) of the vinylacetate reaction unit (13) is supplied to a vinyl acetate separation zone (17), which may be either a condenser, or a washing unit to which a liquid washing agent is supplied as stream (31). A liquid stream (18) comprising vinylacetate, acetic acid, water, optionally washing agent and optional other components (typically heavy components such as acetaldehyde and ethyl acetate) leaves vinylacetate wash zone (17), and is subsequently supplied to vinyl acetate purification zone (19). In purification zone (19), stream (18) is separated into a concentrated vinylacetate stream (26), a concentrated acetic acid stream (27) and one or more streams (28) comprising water, and by-products such as acetaldehyde and ethyl acetate. As mentioned above, all or at least a portion of concentrated acetic acid stream (27) may be used as feed stream (15) for the second (vinylacetate) reaction unit (13). As further shown in FIG. 1, concentrated acetic acid stream (27) may additionally or alternatively be recirculated as washing agent to vinylacetate wash zone (17). A stream (20) comprising ethane, ethylene and carbon dioxide leaving vinylacetate wash zone (17) may be supplied to carbon dioxide removal zone (21) to produce a carbon dioxide stream (21a) and a stream (22) comprising ethane and ethylene depleted of carbon dioxide.

FIG. 2 is a schematic view of a flow scheme for the oxidative hydrogenation of ethylene and production of vinyl acetate, according to another embodiment of the present disclosure. In the flow scheme of FIG. 2, a stream (1) comprising ethane and an oxygen-comprising stream (2) are fed to the first reaction (oxydehydrogenation) unit (3). A stream (4) comprising ethylene, unconverted ethane, acetic acid and water leaves the oxydehydrogenation unit (3), and is supplied to a vapor permeation unit (5) to produce a water vapor stream (7) and a dewatered stream (8) comprising ethylene, ethane and acetic acid. Dewatered stream (8) comprising ethylene, ethane and acetic acid is supplied to second reaction (vinylacetate; "VAM") unit (13), as well as oxygen-containing stream (14). A stream (15) comprising concentrated acetic acid is also supplied to vinylacetate reaction unit (13). This stream (15) comprising concentrated acetic acid may comprise concentrated acetic acid obtained as stream (27) from the vinyl acetate purification section.

The effluent stream (16) of the vinylacetate reaction unit (13) is supplied to a vinyl acetate separation zone (17), which may be either a condenser, or a washing unit to which a liquid washing agent is supplied as stream (31). A liquid stream (18) comprising vinylacetate, acetic acid, water, optionally washing agent and optional other components (typically heavy components such as acetaldehyde and ethyl acetate) leaves vinylacetate wash zone (17), and is subsequently supplied to vinyl acetate purification zone (19). In purification zone (19), stream (18) is separated into a concentrated vinylacetate stream (26), a concentrated acetic acid stream (27) and one or more streams (28) comprising water, and by-products such as acetaldehyde and ethyl acetate. As mentioned above, all or at least a portion of concentrated acetic acid stream (27) may be used as feed stream (15) for the second (vinylacetate) reaction unit (13). If an absorbent is used as washing agent stream (31) for VAM separation zone (17), said absorbent may be recovered as stream (29) from purification zone (19), and at least partially be recycled to washing agent stream (31) for VAM separation zone (17).

As further shown in FIG. 2, concentrated acetic acid stream (27) may additionally or alternatively be recirculated as washing agent to vinylacetate separation (wash) zone (17). A stream (20) comprising ethane, ethylene and carbon dioxide leaving vinylacetate wash zone (17) is supplied to carbon dioxide removal zone (21) to produce a carbon dioxide stream (21a) and a stream (22) comprising ethane and ethylene depleted of carbon dioxide. Stream (22) comprising ethylene and ethane may be (partially) recycled as feed stream (1) for ODH reaction zone (3). Alternatively or additionally, stream (22) comprising ethylene and ethane may be provided to ethane/ethylene separation unit (23) to produce an ethylene-enriched stream (24) and an ethane-enriched stream (25). Ethylene-enriched stream (24) may be withdrawn as saleable product, or may be recycled (not shown) as feed stream to VAM reaction zone (13). The ethane-enriched stream (25) leaving ethane/ethylene separation unit (23) may at least partially be recirculated (not shown) to the first (oxidative dehydrogenation) reaction zone (3).

FIG. 3 is a schematic view of a flow scheme for the oxidative hydrogenation of ethylene and production of vinyl acetate, according to another embodiment of the present disclosure. In the flow scheme of FIG. 3, in addition to the process streams and units already described in FIGS. 1 and 2, it is possible to (partially) by-pass the second (VAM) reaction unit (13) and second separation zone (17), by directly feeding a part or all of the dewatered effluent stream (8) from the vapor permeation unit (5) to vinylacetate separation zone (17) and/or the carbon dioxide removal zone (21) through line (30) and recover acetic acid in purification zone (19). This allows the integrated ODH-VAM system as disclosed herein to (further) produce acetic acid at market specification when the VAM production is not in operation.

It will be clear to the skilled person, that as a schematic diagrams these figures do not show all necessary inputs, outputs, recycle streams, etc. that may be present in the reaction system. Furthermore, in the figures, as will be appreciated, elements can be added, exchanged, and/or eliminated so as to provide any number of additional embodiments. In addition, as will be appreciated, the proportion and the relative scale of the elements provided in the figures are intended to illustrate the embodiments of the present disclosure, and should not be taken in a limiting sense. It should additionally be appreciated that the orientation and configuration shown in FIGS. 1-3 are not intended to be limiting or exhaustive of all possible orientations or configurations, but rather are intended to be merely examples provided to illustrate the spirit of the present disclosure.

In the table below, it is indicated how the "first", "second" etc. streams mentioned in the claims and description correspond to the Arabic numerals in FIGS. 1-3.

| | |
|---|---|
| "first" | 4 |
| "second" | 7 |
| "third" | 8 |
| "fourth" | 16 |
| "fifth" | 18 |
| "sixth" | 20 |
| "seventh" | 27 |
| "eighth" | 26 |
| "ninth" | 22 |
| "tenth" | 25 |
| "eleventh" | 24 |

That which is claimed is:

1. An integrated process for the production of ethylene and vinyl acetate (VAM), comprising
    contacting in a first reaction zone a gas stream comprising ethane and optionally ethylene with an oxygen-containing gas stream in the presence of a oxydehydrogenation catalyst under oxidative dehydrogenation conditions to produce a first product stream comprising ethane, ethylene, acetic acid and water, and optionally other compounds,
    separating said first product stream in a vapor permeation unit into a second stream comprising water and a third stream comprising ethane, ethylene, acetic acid, and optionally other gaseous compounds,
    contacting in a second reaction zone all or at least a portion of said third stream with a stream comprising concentrated acetic acid and with an oxygen-containing gas stream in the presence of a VAM catalyst, to produce a fourth product stream comprising vinyl acetate, acetic acid, ethane, ethylene, water, carbon dioxide, and optionally other compounds,
    separating said fourth product stream in a vinyl acetate separation zone into a fifth stream comprising vinylacetate, acetic acid, water and optionally other condensable compounds, and a sixth stream comprising ethylene, ethane, carbon dioxide and optionally other gaseous compounds, and
    recovering vinyl acetate from said fifth stream.

2. The process according to claim 1, wherein the vinyl acetate separation zone comprises a condenser.

3. The process according to claim 1, wherein the vinyl acetate separation zone is a washing zone, wherein the fourth product stream is contacted with water or a liquid absorbent to produce a fifth stream comprising vinylacetate, acetic acid, water and/or absorbent and optionally other condensable compounds, and a sixth stream comprising ethylene, ethane, carbon dioxide, and optionally other gaseous compounds.

4. The process according to claim 3, wherein said fifth stream is fed to a purification zone to produce a seventh stream comprising concentrated acetic acid, an eighth stream comprising concentrated vinyl acetate, and one or more streams comprising water and/or absorbent, and optionally other compounds.

5. The process according to claim 4, wherein all or at least a portion of the seventh stream comprising concentrated acetic acid is used as the feed stream comprising concentrated acetic acid supplied to the second reaction zone.

6. The process according to claim 3, wherein the sixth stream comprising ethylene, ethane, carbon dioxide, and optionally other gaseous compounds is fed to a carbon dioxide removal zone to remove carbon dioxide and optionally light condensable compounds, to produce an ninth stream enriched in ethane and ethylene.

7. The process according to claim 6, wherein all or at least a portion of said ninth stream enriched in ethane and ethylene is recycled to the first reaction zone.

8. The process according to claim 6, wherein said ninth stream enriched in ethane and ethylene is separated in a ethane/ethylene separation unit to produce a tenth stream enriched in ethane and an eleventh stream enriched in ethylene.

9. The process according to claim 8, wherein all or at least a portion of the tenth stream enriched in ethane is recirculated to the first reaction zone and/or wherein all or at least a portion of the eleventh stream enriched in ethylene is recirculated to the second reaction zone.

10. A reaction system for the oxidative dehydrogenation of ethane and co-production of vinyl acetate, comprising
    a first reaction zone, having
        an inlet for receiving an ethane-containing feed stream,
        an inlet for receiving an oxygen-containing feed stream, and
        an outlet for discharging an effluent from the first reaction zone,
    a vapor permeation unit, having
        an inlet for receiving an effluent from the first reaction zone,
        an outlet for discharging a water-depleted effluent stream from the vapor permeation unit, and
        an outlet for discharging water from the vinyl acetate separation zone,
    a second reaction zone, having
        an inlet for receiving the water-depleted effluent stream from the vapor permeation unit,
        an inlet for receiving an oxygen-containing feed stream,
        an inlet for receiving a concentrated acetic acid-containing feed stream, and
        an outlet for discharging an effluent from the second reaction zone,
    a vinyl acetate separation zone, having
        an inlet for receiving an effluent from the second reaction zone,
        optionally an inlet for receiving a washing liquid stream,
        an outlet for discharging a vinyl acetate-enriched liquid stream from the vinyl acetate separation zone, and
        an outlet for discharging a vinyl acetate-depleted gaseous stream from the vinyl acetate separation zone, a purification zone, having
- an inlet for receiving a vinyl acetate-enriched liquid stream from the vinyl acetate separation zone,
- an outlet for discharging a concentrated acetic acid-containing stream from the purification zone, and,
- an outlet for discharging a concentrated vinyl acetate-containing stream from the purification zone, and
- one or more outlets for discharging further compounds, and optionally, a carbon dioxide removal zone, having
- an inlet for receiving a vinyl acetate-depleted gaseous stream from the vinyl acetate separation zone, and
- an outlet for discharging a carbon dioxide-depleted stream from said carbon dioxide removal zone, and, optionally, an ethane/ethylene separation unit, having
- an inlet for receiving a carbon dioxide-depleted gaseous stream from the carbon dioxide removal zone,
- an outlet for discharging an ethylene-enriched stream from said ethane/ethylene separation unit, and
- an outlet for discharging an ethane-enriched stream from said ethane/ethylene separation unit.

11. The system according to claim 10, which further comprises
- means for recirculating the concentrated acetic acid-containing stream from the purification zone to the second reaction zone, and/or
- means for recirculating an ethylene-enriched stream from the ethane/ethylene separation unit to the second reaction zone, and/or
- means for recirculating an ethane-containing stream from the ethane/ethylene separation unit to the first reaction zone.

12. The system according to claim 10, which further comprises means for by-passing the second reaction zone and vinyl acetate separation zone, said means comprising means for directly feeding the dewatered effluent stream from the vapor permeation unit to the vinyl acetate separation zone and/or carbon dioxide removal zone.

* * * * *